United States Patent [19]

Onwunaka et al.

[11] Patent Number: 5,545,708
[45] Date of Patent: Aug. 13, 1996

[54] THERMOPLASTIC POLYURETHANE METHOD OF MAKING SAME AND FORMING A MEDICAL ARTICLE THEREFROM

[75] Inventors: Theo O. Onwunaka, Midvale, Utah; Mutlu Karakelle, Fort Worth, Tex.

[73] Assignee: Becton, Dickinson and Company, Franklin Lakes, N.J.

[21] Appl. No.: 91,702

[22] Filed: Jul. 14, 1993

[51] Int. Cl.$^6$ .......................... A61M 25/00; C08G 18/32; C08G 18/48; C08G 18/76

[52] U.S. Cl. .............. 528/76; 528/85; 264/165; 604/264; 604/280

[58] Field of Search ............ 528/76, 85; 264/165; 604/264, 280

[56] References Cited

U.S. PATENT DOCUMENTS

| | | | |
|---|---|---|---|
| Re. 31,873 | 9/1989 | Howes | 128/674 |
| 4,058,506 | 11/1977 | Vaeth et al. | 528/65 |
| 4,131,604 | 12/1978 | Szycher | 528/79 |
| 4,156,067 | 5/1979 | Gould | 528/73 |
| 4,273,911 | 6/1981 | Freudenberg et al. | 528/76 |
| 4,386,039 | 5/1983 | Szycher | 528/77 |
| 4,424,335 | 1/1984 | Szycher | 528/77 |
| 4,840,622 | 6/1989 | Hardy | 604/264 |
| 5,004,456 | 4/1991 | Botterbusch | 604/53 |
| 5,070,172 | 12/1991 | Hirai et al. | 528/85 |
| 5,221,788 | 6/1993 | Goto et al. | 528/85 |
| 5,254,662 | 10/1993 | Szycher et al. | 528/67 |

*Primary Examiner*—James J. Seidleck
*Assistant Examiner*—Rabon Sergent
*Attorney, Agent, or Firm*—Arthur D. Dawson

[57] ABSTRACT

A thermoplastic polyurethane having inherent softness properties is formed from a diisocyanate, a polyetherglycol and a mixture of diol chain extenders. The mixture of chain extenders includes a first diol and a second diol which has side chain branching. A method for making the polyurethane of the present invention includes mixing the components to induce an exothermic reaction, followed by curing. The polyurethane formed is suitable for melt processing into medical devices such as catheters, other tubing, hubs and the like.

5 Claims, No Drawings

THERMOPLASTIC POLYURETHANE METHOD OF MAKING SAME AND FORMING A MEDICAL ARTICLE THEREFROM

FIELD OF INVENTION

This invention relates to a thermoplastic polyurethane, and more particularly to a polyurethane having inherent softness properties, a method for making the polyurethane and for forming a medical device therefrom.

BACKGROUND OF THE INVENTION

In the biomedical art area, much research effort is expended to develop and qualify materials for implantation in the body. To be suitable for such applications, a material must not only have physical properties such as strength and flexibility, it should be compatible with the various fluids and enzymes present in the body.

Many types of compounds are used in these applications and polyurethanes are often selected. In general, polyurethanes have a good balance of physical and mechanical properties as well as superior blood compatibility when compared to other polymers such as silicone rubber, polyethylene, polyvinyl chloride and perfluorinated polymers. Some important applications for polyurethanes include peripheral and central venous catheters, coatings for pacemaker leads, drainage devices, implants and the like.

Polyurethanes are synthesized from three basic components, a diisocyanate, a polyglycol and a chain extender, usually a low molecular weight diol, diamine or water. If the extender is a diol, the polyurethane consists entirely of urethane linkages.

Polyurethanes develop microdomaines conventionally termed hard and soft segments, and, as a result, are often referred to as segmented polyurethanes or block copolymers. The hard segments form by localization of the portions of the polymer molecules which include the diisocyanate and the extender components, and are generally highly crystalline. The soft segments form from the polyglycol portions with the diisocyanate of the polymer chains and generally are either amorphous or only partially crystalline. A way of describing the difference between the hard and soft segments may be to consider the components comprising the hard section as a homopolymer having a glass transition temperature ($T_g$) above the normal use temperature range with the components comprising the soft segment as a homopolymer having a $T_g$ below the normal use temperature. Thus the bulk properties of the copolymer are a function of the degree of crystallinity and hard segment content.

Polyurethanes chain extended with diols have been extensively studied for biomedical applications. Representative of such polyurethanes are Vialon® (Beeton, Dickinson and Company), Pellethane® (Upjohn Chemical Co.) and Tecoflex® (Thermedics, Inc.). These commercially available products provide compatibility with physiologic conditions, however, of the compounds cited above, only the Vialon® polyurethane generally does not require processing additives such as antioxidants and detackifiers. The use of these potentially extractable antioxidants and detackifiers is a disadvantage in many biomedical applications. The above cited polyurethanes are thermoplastic, and therefore may be thermoformed using techniques such as extrusion and injection molding.

A material used to form tubing for catheters has two requirements which are in direct conflict with each other. Ideally, the catheter is stiff and smooth to facilitate placement, but once placed, ideally, the catheter is soft, flexible and has a soft tip so that damage to the blood vessel caused by patient and catheter movements is minimized.

A catheter marketed under the tradename Flextip® is produced by Arrow International Corp., Wilm., Del. United States Patents related to the Flextip® product are U.S. Pat No. RE 31,873 to Howes and U.S. Pat. No. 5,004,456 to Botterbusch, which teach a catheter including a relatively soft distal end segment intended for insertion into a body cavity or blood vessel and a relatively hard rigid portion joined to the distal end segment by heat and/or pressure. The Flextip® segments are formed from polyurethanes having an aliphatic or aromatic diisocyanate as a component. Potential drawbacks with catheters having a discrete distal tip section joined to a body portion are the possibility that a separation may occur during use at the junction point between the two components; also there is increased manufacturing complexity associated with forming an additional part, i.e., joining the part to the body portion and testing an additional assembly step.

Several other workers have developed polyurethanes which are substantially stiff and rigid when dry, but upon exposure to a physiological environment will soften and swell. A representative catheter which softens after placement is found in U.S. Pat. No. 4,840,622 to Hardy which teaches tubing design and a material which softens on insertion into the body. According to Hardy the material includes a hydrophilic polyurethane. A drawback related to these catheters which soften with exposure to physiological conditions is that they also swell. Swelling in cross-section may be desirable in some instances, because it increases the inner bore, thus assisting fluid flow. However, swelling also increases length, thus a catheter which is properly placed on insertion may increase in length with softening so that it no longer is properly placed. Additionally in some of the materials which may be used for these applications, the softening rate under physiological conditions may be slow. Thus a procedure may be completed and the catheter removed before the benefit of its softening is realized.

While the above cited and similar teachings have improved the materials and designs available to the art for catheters and other medical devices, there still is a need for materials having an initial stiffness with an inherent softness and flexibility which can be melt processed into medical articles. The present invention addresses this need.

SUMMARY OF THE INVENTION

A thermoplastic polyurethane is formed from a diisocyanate, a polyetherglycol and a mixture of diol chain extenders. The mixture of diol chain extenders includes a first diol and a second diol which has side chain branching. The present polyurethane preferably has a hard segment to soft segment ratio (percent, weight/weight) between about 30:70 to about 60:40. The second diol chain extender desirably includes a branched chain diol having the structure

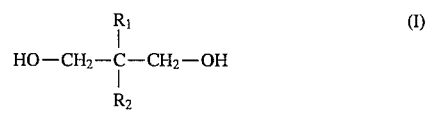

and wherein $R_1$ is a saturated alkyl group with from one to six carbon atoms and $R_2$ is selected from the group including hydrogen and a saturated alkyl group with from one to six carbon atoms. Preferably the second diol chain extender has $R_1$ as a butyl group and $K_2$ as an ethyl group. The mixture of diol chain extender may have a ratio (percent, equivalents/equivalents) between the first diol chain extender to the second diol chain extender between about 90:10 to about 10:90.

A method for making the present polyurethane includes combining with effective mixing, a diisocyanate, a polyetherglycol and a mixture of diol chain extenders at a temperature sufficient to induce an exotherm and give a substantially uniform melt of a polyurethane and then curing the polyurethane.

A catheter tubing of the present invention includes a thermoplastic polyurethane formed from the reaction product of a diisocyanate, a polyetherglycol and a mixture of a first diol chain extender and a second diol chain extender which has side chain branching. The present polyurethane preferably has a hard segment to soft segment ratio (percent, weight/weight) between about 30:70 to about 60:40. The second diol chain extender desirably includes a branched chain diol having the structure (I) as set out above.

A method for making a catheter tubing of the present invention includes forming a polyurethane of the present invention by combining with mixing a polyetherglycol, a diisocyanate and a mixture of diol chain extenders at a temperature sufficient to induce an exotherm and give a substantially uniform melt of the polyurethane. The resultant viscous liquid polyurethane is then cured and convened into chips suitable for melt forming. The polyurethane chips are then melt formed into tubing for a catheter. The polyurethane of the present invention thus formed has a hard segment to soft segment ratio range (percent, weight/weight) between about 30:70 to about 60:40. The mixture of diol chain extenders preferably includes a first chain extender and a second chain extender ranges (percent, equivalents/equivalents) between about 90:10 to about 10:90. The second chain extender desirably includes a branched chain diol having the structure (I) as set out above. The mixture of chain extenders may have a ratio range (percent, equivalents/equivalents) between the first diol chain extender between about 90:10 to about 10:90.

A catheter formed from a polyurethane of the present invention has a tensile strength which compares favorably with current commercial polyurethanes such as Vialon®. Additionally the present polyurethane has an inherent softness due to the presence of the side chain branching in the mixture of chain extenders. The present invention offers advantages over the other commercial polyurethanes such as Tecoflex® and Pellethane® because the softness is achieved without the presence of potentially leachable low molecular weight additives. Further, the initial stiffness and final flexibility and softness may be adjusted by formulation adjustment.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

In accordance with the present invention, a polyurethane of the present invention is thermoplastic and melt processable into medical devices such as catheters and other medical devices such as adapters, intravenous tubing, needle hubs, lancets and the like, where exposure to physiological conditions is required.

A thermoplastic polyurethane of the present invention includes the reaction product of a diisocyanate, a polyetherglycol and a mixture of diol chain extenders including an aliphatic diol having branched side chains.

Usable diisocyanates include aromatic and non-aromatic diisocyanates. Suitable aromatic diisocyanates include but are not limited to 4,4'-diphenylmethane diisocyanate (MDI), toluene diisocyanate (TDI), 3,3'-diphenylmethane diisocyanate, 1,4-phenylene diisocyanate and 3,3'-diethyl- 4,4'-biphenyl diisocyanate. Suitable non-aromatic diisocyanates include but are not limited to 1,12-dodecanediisocyanate, 1,11-undecanediisocyanate, 1,10-decanediisocyanate, 1,9-nonanediisocyanate, 1,8-octanediisocyanate, 1,7-heptanediisocyanate, 1,6-hexanediisocyanate and trimethyl-1,6-hexanediisocyanate. A preferred diisocyanate is MDI.

Suitable polyethergylcols include but are not limited to polyetherglycols having molecular weights between about 500 and 8000 such as polyethylene oxide, polypropylene oxide and polytetramethylene ether glycol (PTMEG). Preferably, the polyetherglycol is PTMEG with a molecular weight of about 1000.

Suitable chain extenders include but are not limited to a mixture including a first diol such as butane diol, ethylene glycol, diethylene glycol, triethylene glycol, 1,2-propane diol, 1,3-propane diol, 1,6-hexane diol, 1,4-bis hydroxymethyl cyclohexane and hydroquinone dihydroxyethyl ether. Preferably the first diol is butane diol (BDO). A second diol in the mixture desirably has side chain branching and the structure

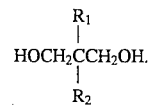

Desirably, $R_1$ is a saturated alkyl group having from one to about six carbon atoms and $R_2$ is selected from the group including hydrogen or a saturated alkyl group having from one to about six carbon atoms. The $R_1$ and $R_2$ groups may be the same or different. Preferably $R_1$ is a butyl group and $R_2$ is an ethyl group (2-butyl-2-ethyl-1,3-propanediol, {BEPD }).

The ratio range (equivalents/equivalents, [eq./eq.]) of the first chain extender to the second chain extender may be between about 10:90 to about 90:10. When the first diol is BDO and the second diol is BEPD, a preferred ratio of BDO/BEPD is about 50:50. The equivalent weight (eq. wt.) of a compound is the molecular weight divided by the number of reactive moieties present on the molecule (e.g., the eq. wt. of a diol is the molecular weight in grams divided by 2). The number of equivalents (eq.) present in a given amount of a material is the mass in grams divided by the eq. wt.

In this description, the percentage hard segment (HS) is calculated based on the diisocyanate and extender (i.e., the mass of the chain extender plus the mass of the diisocyanate divided by the total mass of the reactants used times 100). The HS to soft segment (SS) ratio of the polyurethane of the present invention may range between about 30:70 to about 60:40 with a ratio generally about 50:50 being preferred.

It is believed that the presence of side chain branching in the mixture of the chain extenders, which is included in the HS, tends to disrupt the linearity of the HS. In a polyurethane which utilizes only a single chain extender, the HS tends to be highly crystalline and rigid. In the present invention, the side chain branching of the second chain extender is believed to introduce mobility, hence flexibility, into the HS by disrupting the linearity and the packing in the HS and reduces the differentiation between the HS and SS. This reduced differentiation between the HS and SS leads to a reduction in the initial bend force or stiffness for the present polyurethane when compared to many commercial polyurethanes at comparable HS.

The present polyurethane is preferably prepared from a mixture of diol chain extenders. The following examples are provided to further illustrate the invention but are not to be considered as limitative of the invention.

EXAMPLE I

General procedure for synthesis

In a well stirred reactor vessel, PTMEG- 1000, MDI and chain extender were combined with effective mixing at room temperature. As used herein, the term "effective mixing" describes thoroughly mixing the components without substantial aeration. An exotherm to about 100° C. develops and stirring is continued for up to about three minutes. The resulting viscous mixture is then maintained at about 125° C. for about one hour to ensure a substantially complete cure. The resultant polyurethane is then allowed to cool forming a rigid resin which is then chipped to a size suitable for melt forming.

Table I displays the components of a series of polyurethanes of the present invention prepared according to the procedure of Example I. The series includes several BEPD/BDO ratios at about fifty percent hard segment. These exemplary polyurethanes of the invention were prepared for extrusion, injection molding and physical property testing. The mass of each component is given in grams and the number of equivalents is shown. The preferred reagents may be obtained from the listed sources. As is known to one skilled in the synthesis of polymers, high reagent purity levels are essential for formation of high molecular weight product. In all cases, the materials are substantially free of water and have purity suitable for polymerization.

| Component | Source |
|---|---|
| Butane diol (BDO) | Aldrich, Milwaukee, WI |
| Polytetramethylene ether glycol (PTMEG) | DuPont, Wilmington, DE |
| 2-butyl-2-ethyl-1,3-propane diol (BEPD) | Kodak, Rochester, NY |
| 4,4'-diphenylmethanediisocyanate (MDI) | Mobay, Pittsburgh, PA |

TABLE I

| Sample No./ (% HS) | Ratio BEPD/ BDO | g.(Eq.)BEPD/ g.(Eq.)BDO | g(Eq.) PTMEG | g.(Eq.)MDI |
|---|---|---|---|---|
| 1(51.5) | 0/100 100% BDO | 76.6(1.70) | 363.8(0.73) | 309.7(2.47) |
| 2(51.9) | 10/90 | 13.6(0.17)/ 68.9(1.53) | 360.8(0.72) | 306.8(2.45) |
| 3(52.3) | 20/80 | 27.3(0.34)/ 61.25(1.36) | 357.8(0.72) | 303.4(2.43) |
| 4(52.7) | 30/70 | 40.9(0.51)/ 53.6(1.19) | 354.8(0.71) | 300.8(2.33) |
| 5(53.1) | 40/60 | 54.5(0.68)/ 45.9(1.02) | 351.8(0.70) | 297.9(2.38) |
| 6(53.5) | 50/50 | 68.2(0.85)/ 38.3(0.85) | 348.8(0.70) | 294.8(2.36) |
| 7(51.5) | 100/0 100% BEPD | 113.3(1.41) | 363.8(0.73) | 273.0(2.18) |

Sixteen gauge (16 g/0.139"OD×0.77"ID) 1.73 mm×1.02 mm tubing was extruded from chips of each of the several polyurethanes of Table I. The tubing was extruded using a 2.54 cm extruder at temperatures between about 180° to about 225° C. The extrusion was successful in all cases, with transparent tubing being produced in examples #1 and 4–7. Examples #2 and 3 produced opaque tubing. Tensile bars were successfully injection molded from all seven polyurethanes.

Tubing and tensile bars of the several polyurethanes from Table I were subjected to stiffness, hardness and tensile strength testing. Table II gives the ultimate tensile strength and the elongation at break for the several polyurethanes. Example #1, which has 100% BDO as a chain extender, is representative of a commercial polyurethane used for catheter tubing.

TABLE II

| Number | Ratio-BEPD/BDO | Tensile (psi) | % Elongation |
|---|---|---|---|
| 1 | 0/100 | 7,800 | 456 |
| 2 | 10/90 | 8,192 | 410 |
| 3 | 20/80 | 6,393 | 434 |
| 4 | 30/70 | 9,249 | 330 |
| 5 | 40/60 | 9,418 | 320 |
| 6 | 50/50 | 10,843 | 354 |

Table III shows the Shore Hardness values determined on the several polyurethanes from Table I.

TABLE III

| Number | Ratio-BEPD/BDO | Shore "A" | Shore "D" |
|---|---|---|---|
| 1 | 0/100 | 90.4 | 45.5 |
| 2 | 10/90 | 88.3 | 44.1 |
| 3 | 20/80 | 89.5 | 44.1 |
| 4 | 30/70 | 85.0 | 40.4 |
| 5 | 40/60 | 81.9 | 34.3 |
| 6 | 50/50 | 74.0 | 31.3 |
| 7 | 100/0 | 67.7 | 26.6 |

Table IV shows a stiffness determination made on a two inch segment (equilibrated at 23° C. and 45% relative humidity) of the 16 gauge tubing prepared from the several polyurethanes of Table I. Stiffness is measured by clamping a tubing section across its longitudinal axis at the ends and applying an axial load to cause the tube to deflect. The bend force in grams required to cause the tube to deflect is a measure of stiffness.

TABLE IV

| Number | Ratio-BEPD/BDO | Bend Force (grams) |
|---|---|---|
| 1 | 0/100 | 57.3 |
| 2 | 10/90 | 39.9 |

TABLE IV-continued

| Number | Ratio-BEPD/BDO | Bend Force (grams) |
|--------|----------------|--------------------|
| 3 | 20/80 | 32.3 |
| 4 | 30/70 | 17.5 |
| 5 | 40/60 | 11.9 |
| 6 | 50/50 | 9.1 |

The results presented in the Tables II–IV show that the several polyurethanes of the present invention prepared at about 50% HS are comparable to the commercial polyurethane, as represented by example #1 currently used for catheters, in tensile strength, but are significantly softer and less stiff. Table III shows that the hardness decreases as the amount of BEPD in the mixture of chain extenders is increased. Table IV shows that the bend force (stiffness) decreases as the amount of BEPD in the mixture increases. At all levels of BEPD, the ultimate tensile strength is comparable to the ultimate tensile strength of the commercial (#1) material. This is contrary to the normal expectation that, in general, soft and less stiff materials have lower ultimate tensile strength than harder and stiffer materials.

The extruded tubing of the present invention has a low surface tack. Tubing of the present invention, when tied in a knot, is easily unloosened. This property suggests a resistance to kinking. Tubing of similar softness prepared from current commercial polyurethanes requires a lower HS component or potentially leachable additives to achieve comparable softness, and as a result, has higher surface tack than the present polyurethane.

A method for producing a polyurethane of the present invention includes thoroughly mixing a diisocyanate, a polyetherglycol and a mixture of diol chain extenders in proportions predetermined in accordance with the desired HS/SS ratio. If the reaction does not start spontaneously, the reaction mixture may be heated sufficiently to induce an exotherm. Once the exotherm has occurred and the temperature begins to decline, the stirring preferably is continued for about three minutes. The resultant viscous homogenous melt may then advantageously be removed from the reactor vessel prior to curing.

Any conventional method may be used to effect curing. The viscous liquid is simply set aside for a suitable time at a suitable temperature, as, for example from ambient to about 130° C. and for about one hour to about two weeks. Preferably the temperature is about 125° C. and the time is about one hour. Following curing, the polyurethane is allowed to cool to room temperature, generally becoming a rigid resin, and preferably chipped to a size suitable for melt processing.

The polyurethanes of the present invention may be formed into desired shapes by a variety of thermoforming processes such as sheet forming, extrusion, injection molding and the like. The particular technique may be selected based on the desired application. Preferably when a catheter tubing is desired, an extrusion process is selected. One skilled in the art of extrusion will appreciate that the particular extruder settings are dependent on the composition of the material being extruded, the design (i.e., the wall thickness and size, etc.) of the product being produced, the throughput and the equipment being used. Representative polyurethanes of the present invention were satisfactorily extruded and injection molded, providing samples for evaluation. The softness and flexibility demonstrated by these samples were inherent to the compound, not requiring any additional low molecular weight plasticizers or stabilizers. Additionally, because these were obtained with a HS content about 50 percent, the well documented (W.Lemm, Polyurethanes in Biomedical Engineering, edited by H. Planch, G. Eibers and I. Syre; Elsevier Science Publishers (1984); pp. 103–109) effect of low (30–50 percent) HS content on biodegradation is avoided. The above identified Lemm reference and the additional references contained therein suggest that much of the biodegradation in polyurethanes occurs in the SS, thus low HS content increases the number of sites available for enzymatic attack and hydrolysis.

What is claimed is:

1. A catheter tubing formed from thermoplastic polyurethane consisting essentially of the reaction product of a diisocyanate, a polyetherglycol and a mixture of chain extenders, said mixture of chain extenders consisting essentially of butane diol and 2-butyl 2-ethyl propane 1,3-diol, said polyurethane having a hard segment to soft segment ratio (percent, weight/weight) between about 30:70 and 60:40.

2. The catheter tubing of claim 1 wherein said polyetherglycol has a molecular weight between about 500 and about 8000 and is selected from the group consisting of polyethylene oxide glycol, polypropylene oxide glycol and polytetramethylene ether glycol.

3. The catheter tubing of claim 1 wherein said polyetherglycol is polytetramethylene ether glycol having a molecular weight about 1000.

4. The catheter tubing claim 1 wherein said diisocyanate is an aromatic diisocyanate selected from the group consisting of 4,4'-diphenylmethane diisocyanate, 2,2'-dimethyl-4,4'-biphenyldiisocyanate and 3,3'-dimethyl-4,4'-biphenyl diisocyanate.

5. A method for making a catheter tubing comprising:

combining 4,4'-diphenylmethane diisocyanate, a polyetherglycol having a molecular weight between about 500 and about 3000 selected from the group consisting of polyethylene oxide glycol, polypropylene oxide glycol and polytetramethylene oxide glycol; and a mixture of diol chain extenders, said mixture consisting essentially of butane diol as a first component and a second component having the structure

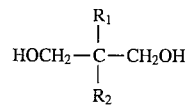

wherein said $R_1$ group is a butyl group, said $R_2$ group is an ethyl group, and said mixture having a ratio of said first chain extender to said second chain extender ranging between about 90:10 to 10:90 (percent, equivalents/equivalents) at a temperature sufficient to induce an exothermic reaction to give a substantially uniform melt of a polyurethane having a hard segment to soft segment ratio (percent, weight/weight) between about 30:70 to about 60:40;

curing said polyurethane;

convening said polyurethane into chips suitable for melt forming; and melt forming said polyurethane into tubing for catheters.

* * * * *